United States Patent
Moulton et al.

(10) Patent No.: US 11,998,694 B2
(45) Date of Patent: *Jun. 4, 2024

(54) FACEMASK SEAL

(71) Applicant: Sleepnet Corporation, Hampton, NH (US)

(72) Inventors: Thomas M. Moulton, Rye, NH (US); Jerry J. Gong, Andover, MA (US)

(73) Assignee: Sleepnet Corporation, Hampton, NH (US)

( * ) Notice: Subject to any disclaimer, the term of this patent is extended or adjusted under 35 U.S.C. 154(b) by 152 days.

This patent is subject to a terminal disclaimer.

(21) Appl. No.: 17/225,239

(22) Filed: Apr. 8, 2021

(65) Prior Publication Data

US 2021/0220595 A1  Jul. 22, 2021

Related U.S. Application Data

(63) Continuation of application No. 16/295,710, filed on Mar. 7, 2019, now Pat. No. 10,974,007.

(51) Int. Cl.
*A61M 16/06* (2006.01)
*A41D 13/11* (2006.01)
(Continued)

(52) U.S. Cl.
CPC ..... *A61M 16/0605* (2014.02); *A41D 13/1161* (2013.01); *A62B 18/025* (2013.01); *A62B 18/08* (2013.01)

(58) Field of Classification Search
CPC ............ A61M 16/0048; A61M 16/047; A61M 16/0611; A61M 16/0616; A61M 16/0622;
(Continued)

(56) References Cited

U.S. PATENT DOCUMENTS 4,060,855 A   12/1977   Rappleyea
4,677,977 A   7/1987   Wilcox
(Continued)

FOREIGN PATENT DOCUMENTS

EP   1057494 A2   12/2000
WO   97/09090 A1   3/1997
(Continued)

OTHER PUBLICATIONS

Extended European Search Report for European Application No. EP20766872.4 dated Nov. 4, 2022, 8 pages.

*Primary Examiner* — Justine R Yu
*Assistant Examiner* — Alexander Morales
(74) *Attorney, Agent, or Firm* — Pierce Atwood LLP; Christopher A. Baxter

(57) ABSTRACT

The present disclosure relates to an improved sealing element for a facemask. The sealing element includes three primary faces: a facemask attachment face; a skin contact face; and a third face. The skin contact face is the longest of the three primary faces when the sealing element is viewed in cross-section. The third face extends from a plane defined by an attachment surface of a corresponding facemask. When the sealing element is viewed in cross-section, the third face has a length that is less than 90% of a length of the skin contact face. Moreover, an entirety of the third face is configured to form a portion of the corresponding facemask's chamber when the facemask is worn by a user.

18 Claims, 8 Drawing Sheets

(51) Int. Cl.
*A62B 18/02* (2006.01)
*A62B 18/08* (2006.01)

(58) Field of Classification Search
CPC .. A61M 2016/0661; A61M 2205/0216; A61M 2205/0238; A61M 2210/0625; A61M 16/0633; A61M 16/0638; A61M 16/0644; A61M 16/065; A61M 16/0655; A62B 18/02
USPC .................................................. 128/206.24
See application file for complete search history.

(56) References Cited

U.S. PATENT DOCUMENTS

| | | | |
|---|---|---|---|
| 5,518,802 A * | 5/1996 | Colvin | B32B 3/12 |
| | | | 428/72 |
| 5,647,357 A | 7/1997 | Barnett et al. | |
| 6,631,718 B1 | 10/2003 | Lovell | |
| 6,701,925 B1 | 3/2004 | Resnick | |
| 7,219,670 B2 * | 5/2007 | Jones, Jr. | A61M 16/208 |
| | | | 128/205.25 |
| 7,243,650 B2 | 7/2007 | Thornton | |
| 7,308,895 B2 | 12/2007 | Wixey et al. | |
| 8,490,623 B2 | 7/2013 | Berthon-Jones et al. | |
| 8,596,273 B2 | 12/2013 | Burz et al. | |
| 8,869,798 B2 * | 10/2014 | Wells | A61M 16/0622 |
| | | | 128/206.24 |
| 9,119,929 B2 * | 9/2015 | McAuley | A61M 16/06 |
| 9,132,255 B2 * | 9/2015 | Skipper | A61M 16/0605 |
| 10,188,820 B2 | 1/2019 | Edwards et al. | |
| 10,786,642 B2 * | 9/2020 | Biener | A61M 16/06 |
| 10,974,007 B2 * | 4/2021 | Moulton | A41D 13/1161 |
| 10,987,477 B2 * | 4/2021 | Law | A62B 18/02 |
| 2004/0118406 A1 | 6/2004 | Lithgow et al. | |
| 2008/0011303 A1 | 1/2008 | Angadjivand et al. | |
| 2008/0230068 A1 | 9/2008 | Rudolph | |
| 2008/0257354 A1 * | 10/2008 | Davidson | A61M 16/06 |
| | | | 128/206.24 |
| 2015/0246198 A1 * | 9/2015 | Bearne | A61M 16/0611 |
| | | | 128/205.25 |
| 2017/0128689 A1 | 5/2017 | Law et al. | |
| 2017/0173371 A1 * | 6/2017 | Truex | A62B 18/02 |
| 2018/0008848 A1 | 1/2018 | Moulton et al. | |

FOREIGN PATENT DOCUMENTS

| | | |
|---|---|---|
| WO | 00/20072 A1 | 4/2000 |
| WO | 2009062265 A1 | 5/2009 |
| WO | 2013006913 A1 | 1/2013 |
| WO | 2017070351 A1 | 4/2017 |
| WO | 2018009353 A1 | 1/2018 |

* cited by examiner

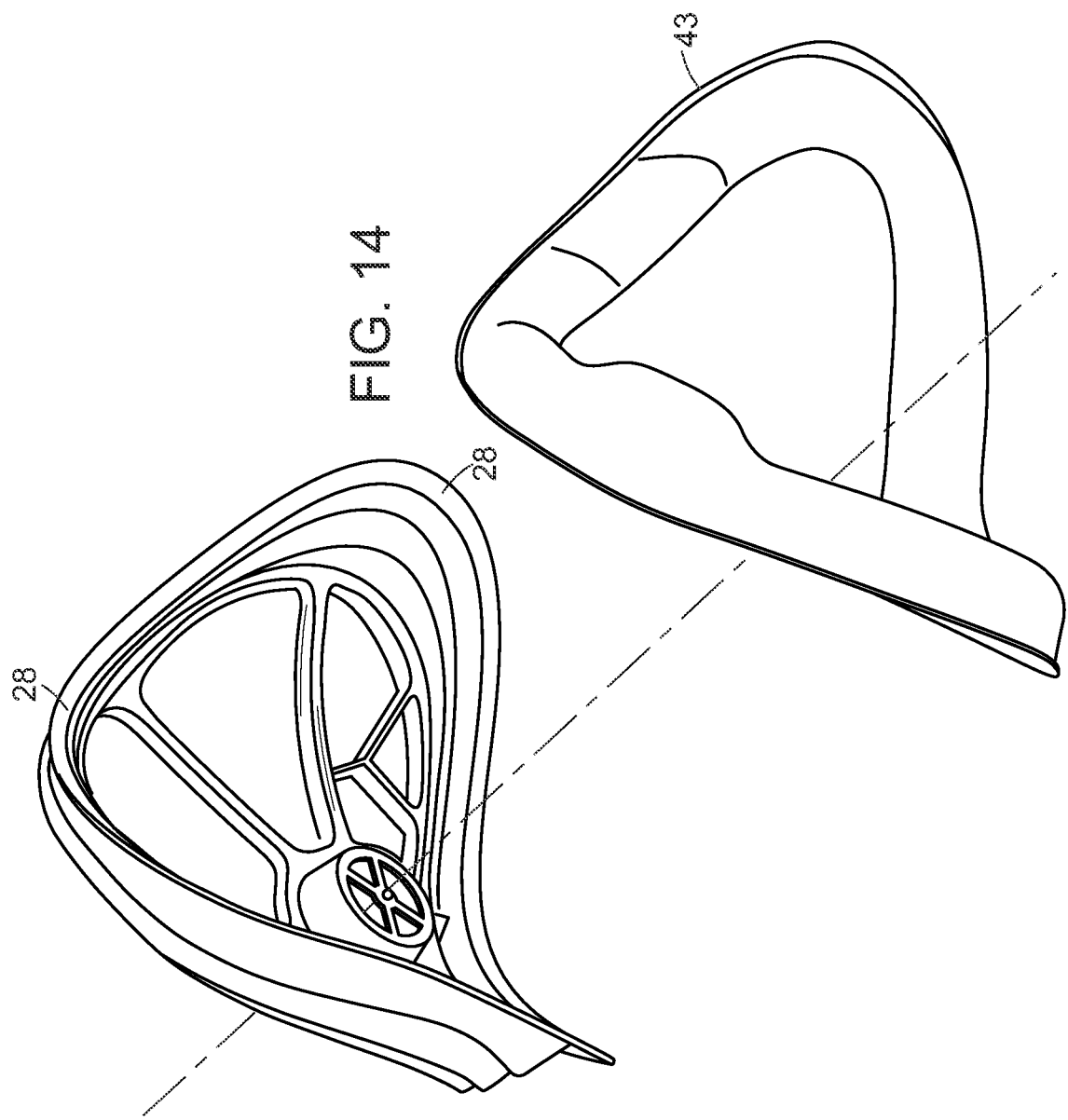

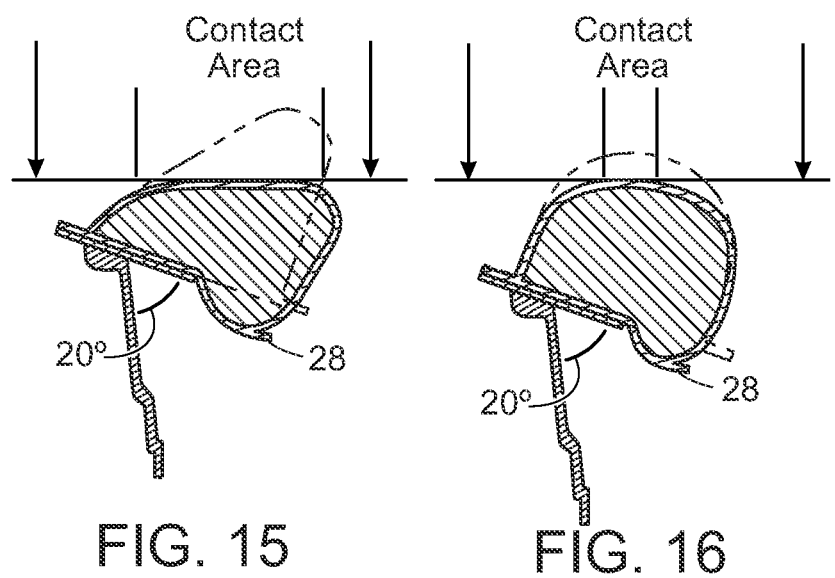

FACEMASK SEAL

BACKGROUND

Facemasks are used in a variety of context for the purpose of sealing the face, or a portion thereof, from an external environment. A variety of facemask seals are known in the art. An example of a popular facemask seal, and one referred to herein as "a prior art seal" or "the prior art seal" is described below and shown diagrammatically in FIG. 1.

While the prior art seal performs in a satisfactory manner, and is comfortable to a user, leakage can be experienced, particularly in certain areas which are known to be difficult to seal. Such areas include, for example, areas around the nose and the bridge of the nose.

SUMMARY

Disclosed are instances of a sealing element for sealing an air gap between the face of a user and a facemask, the sealing element comprised of a formed flexible material having a durometer value of 60 or less on a Type 000 scale, the sealing element having at least three primary external faces comprising: a) a facemask attachment face; b) a skin contact face; and c) a third face wherein, when viewed in cross-section, the skin contact face is the longest of the three faces. Also disclosed are instances of the sealing element of as described above wherein the formed flexible material comprises a sealed, flexible external membrane bladder containing a fluid or a gel. Disclosed are instances of the sealing element described above wherein the external membrane bladder is formed from a thermopolymer and the gel is a silicone gel. Disclosed are instances of the sealing element described above wherein the external membrane bladder is formed by bonding a first and a second thermopolymer sheet portion. Also disclosed are instances of the sealing element described above wherein the first thermopolymer sheet portion is drawn under heat and vacuum to form the skin contact face and the third face. Disclosed are instances of the sealing element described above wherein, when viewed in cross section, the side corresponding to the third face has a length which is less than about 70%-90% of the length of the skin contact face. Further disclosed are instances of the sealing element described above further comprising one or more local lobe domains having an extended skin contact face and an extended third face, as compared with adjacent non-lobe portions, for the purpose of sealing areas of substantial variation in the facial structure of the user. Disclosed are instances wherein the one or more local lobe domains comprise an upper portion and a lower portion, wherein the lower portion is generally rectangular in shape, the height of the rectangle approximating the height of adjacent, non-lobe portions of the sealing element; and the upper portion is generally trapezoidal in shape, wherein the angled sides of the trapezoid form an average angle of between 30 degrees and 89 degrees with the top of the rectangular lower portion. Further disclosed are instances of the sealing element described above wherein the angle formed between the attachment face and the third face is between 70 degrees and 90 degrees.

Further disclosed are instances of a facemask comprising: a) a housing defining a facemask chamber, the housing comprising a continuous attachment flange; and b) a sealing element adhesively attached to the attachment flange and configured to form a seal between the attachment flange of the housing and the face of a user, the sealing element comprised of a formed flexible material having a durometer value of 60 or less on a Type 000 scale, the sealing element having at least three primary external faces comprising: i) a facemask attachment face; ii) a skin contact face; and iii) a third face, wherein, when viewed in cross-section, the skin contact face is the longest of the three faces. Also disclosed are instances of the facemask wherein the attachment flange slopes inwardly along at least a majority of its surface length. Further disclosed are instances of the facemask described above wherein the formed flexible material comprises a sealed, flexible external membrane bladder containing a fluid or a gel. Also disclosed are instances of the facemask as described above wherein the external membrane bladder is formed from a thermopolymer and the gel is a silicone gel. Disclosed are instances of the facemask described above wherein the external membrane bladder is formed by bonding a first and a second thermopolymer sheet portion. Disclosed are instances of the facemask described, wherein the first thermopolymer sheet portion is drawn under heat and vacuum to form the skin contact face and the third face. Further disclosed are instances of the facemask described wherein, when the bladder is viewed in cross section, the side corresponding to the third face has a length which is less than about 70%-90% of the length of the skin contact face. Described are instances of the facemask described above further comprising one or more local lobe domains having an extended skin contact face and an extended third face, relative to adjacent non-lobe domains, for the purpose of sealing areas of substantial variation in the facial structure of the user. Disclosed are instances of the facemask described above wherein the majority of the surface of the attachment flange slopes inwardly at least 5 degrees. Also disclosed are instances of the facemask described above wherein the majority of the surface of the attachment flange slopes inwardly from about 15 degree to about 30 degrees. Disclosed are instances of the facemask described above wherein the surface area of the seal formed between the skin contact face of the sealing element and the face of the user is greater than the surface area formed by an otherwise identical facemask having a semi-circular sealing element of substantially identical height. Also disclosed are instances of the facemask described above wherein the surface area of the seal formed between the skin contact face of the sealing element and the face of the user is greater than the surface area formed by an otherwise identical facemask having a semi-circular sealing element of substantially identical volume. Disclosed are instances of the facemask described above wherein the angle formed between the attachment face and the third face is between 70 degrees and 90 degrees.

BRIEF DESCRIPTION OF THE FIGURES

FIG. 14 shows an exploded perspective view of a facemask exposing an instance of the attachment flange.

FIG. 15 is a diagrammatic cross-sectional representation of an instance of the seal of the present disclosure making contact with a user's face.

FIG. 16 is a diagrammatic cross-sectional representation of an instance of the prior art seal making contact with the skin of a user's face.

DETAILED DESCRIPTION

The present disclosure is directed toward a new and non-obvious improvement in a sealing element for sealing the air gap between the face of a user and a facemask. The present disclosure is also related to a facemask comprising the sealing element of the present disclosure. In the context of the present disclosure a "facemask" is defined as a mask sized to fit over a user's nose (nasal mask), a mask sized to fit over a user's nose and mouth (but not eyes and chin), a mask sized to fit over a user's nose, mouth and eyes (but not chin) and a mask sized to fit over a user's nose, mouth, eyes and chin. In a preferred instance, the facemask is a mask that fits over a user's nose and mouth. Any type of facemask falls within the scope of the present disclosure. Exemplified is a dust mask with support ribs for supporting a replaceable filter element (not shown). The full scope of the disclosure extends to any mask worn over the face for the purpose of sealing out the external environment. This includes, for example, all forms of respiratory masks including continuous positive airway pressure (CPAP) masks.

As mentioned above, while the prior art seal performs in a satisfactory manner, and is comfortable to a user, leakage can be experienced, particularly in certain areas which are known to be difficult to seal. Such areas include, for example, areas around the nose and the bridge of the nose. The facemask seal of the present disclosure has been shown to perform in a superior manner, while having otherwise similar characteristics (e.g., comfort, cost, weight, shelf life, etc.).

The sealing element of the present disclosure can be comprised of one or more formed flexible materials having a durometer value of 60 or less on a Type 000 Shore scale; a durometer value of 50 or less on a Type 000 Shore scale; a durometer value of 40 or less on a Type 000 Shore scale; a durometer value of 30 or less on a Type 000 Shore scale; a durometer value of 20 or less on a Type 000 Shore scale or a durometer value of 10 or less on a Type 000 Shore scale. Exemplary formed flexible materials suitable for use in the sealing element of the present disclosure are, for example, silicone gel bladder, air filled bladder, foam (of various types known to one of ordinary skill in the art) and rubber (natural or synthetic).

The Shore durometer is a device known to one of ordinary skill in the art for measuring the hardness of a material, typically of polymers, elastomers, and rubbers. Higher numbers on the scale indicate a greater resistance to indentation and thus harder materials. Lower numbers indicate less resistance and softer materials. The term is also used to describe a material's rating on the scale, as in an object having a "'Shore durometer of 90." Shore durometers are designed to measure specific scale ranges. A Type 000 durometer measures the hardness of very soft materials.

Figure 2:
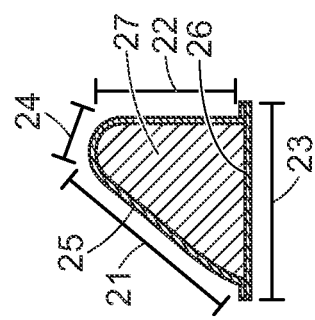
FIG. 2 shows a cross-sectional view of an example the sealing element of the present disclosure taken along line 2-2 of FIG. 13

Instances of the sealing element 43 of the present disclosure comprises at least three primary external faces as shown in FIG. 2. Describing instances of the disclosure in cross-section, the skin contact face 21 is always the longest face. The attachment face 23 can be longer than, shorter than or equal in length to the third face 22. In preferred instances, the third face 22 has a length which is less than about 70% to 90% of the length of the skin contact face 21. In instances of the triangular seal of the present disclosure, the angle formed between the attachment face 23 and the third face 22 is between 70 degrees and 90 degrees. As will be discussed below, for manufacturing reasons, a range of between 70 degrees and 89 degrees is preferred.

Figure 3:
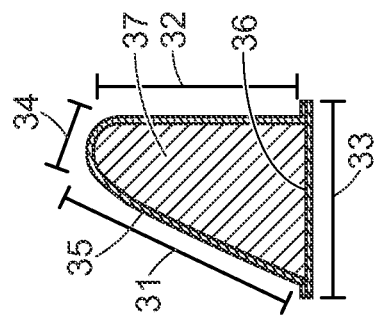
FIG. 3 shows a cross-sectional view of an instance of a local lobe domain of the sealing element of the present disclosure taken along line 3-3 of FIG. 13.
Figure 4:
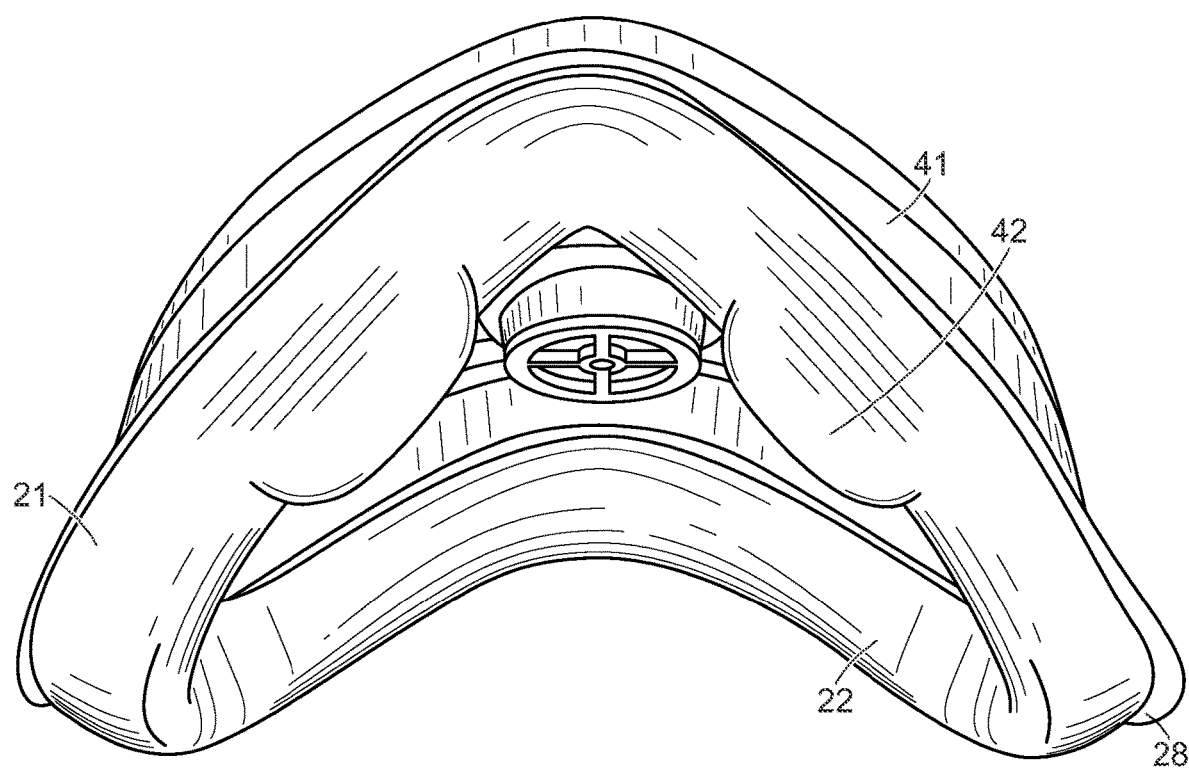
FIG. 4 shows a top perspective view of a facemask with an instance of the sealing element of the present disclosure mounted on the attachment flange. Two local lobe domain instances are also shown.

Further still, the third face 22 occupies the inner perimeter of the sealing element and the skin contact face 21 occupies the outer perimeter of the sealing element, as shown in FIG. 4. In cross-section, the transition between the faces of the triangle of the sealing element of the present disclosure, particularly the transition (24 in FIGS. 2 and 34 in FIG. 3) between the third face and the skin contact face, appear rounded, slightly rounded or even flat. The reason for the rounded or even flat nature of this transition will become clear following consideration of a preferred manufacturing process described below.

In other instances, the sealing element of the present disclosure can have more than 3 primary faces. One skilled in the art will recognize, for example, that a trapezoidal seal will offer many of the advantages described herein in connection with a triangular instance, and one skilled in the art, guided by the present disclosure, can make and use such trapezoidal seals using no more than routine experimentation.

Figure 1:
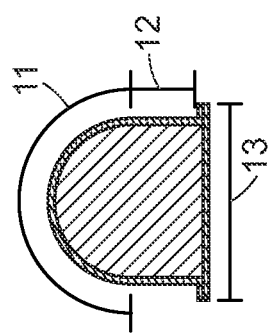
FIG. 1 shows a cross-sectional view of a sealing element of the prior art taken along line 1-1 of FIG. 11.

In comparison, a prior art sealing element, as shown in FIG. 1, has the shape of a modified semi-circle. A modified semi-circle, as defined herein, is a half or semi-circle shape 11 extending from a rectangular base 12. The prior art sealing element also has an attachment face 13 for attachment to a mask.

In one instance of the present disclosure, the formed flexible material of the sealing element comprises an external membrane bladder (FIGS. 2, 25 & 26 and FIGS. 3, 35 & 36) containing a fluid or gel (FIG. 2, 27 and FIG. 3, 37). In an instance of the present disclosure, the external membrane bladder is formed from one or more thermopolymer sheets (for example, 25 and 26 in FIG. 2). Thermopolymer sheet material is known to one of ordinary skill in the art. Examples of such materials include sheets comprising urethane, polyurethane, latex, nitrile and other natural polymers and synthetic polymers. The bladder may be formed from a sheet of thermopolymer comprising, for example, a first and a second thermopolymer sheet portion. The term "thermopolymer sheet portion" is defined to mean a portion of a single sheet folded or otherwise manipulated to form more than one face of the three faces of the sealing element of the present disclosure. Thus, a sheet of thermopolymer material may comprise one or more thermopolymer sheet portions. As can be seen in FIG. 2, for example, attachment face 23 is bounded by a thermopolymer sheet and skin contact face 21 and third face 22 are bounded by a second thermopolymer sheet.

In one instance, the bladder is formed by drawing a first thermopolymer sheet portion into a molding apparatus with heat and vacuum to form the skin contact face and the third face of the sealing element of the present disclosure. A molding apparatus is, in its simplest form, a vacuum mold having a cavity or well in the shape of the skin contact face and third face of the sealing element of the present disclosure. Again, referring to FIG. 2 for example, in a first step, a polymer sheet is heated and drawn under vacuum to form the exterior bladder boundary of the skin contact face 21 and the third face 22. The vacuum is created through the use of air holes in the bottom of the mold cavity. Because the skin contact face 21 and the third face 22 meet at the bottom of the heated vacuum cavity, the transition between those faces tends to be rounded, thereby enabling removal of the molded product and generally facilitating the process. In instances, a gel is then poured into the mold to fill the cavity formed by the first polymer sheet. A second polymer sheet (or another portion of the same polymer sheet) is overlaid on the gel-filled cavity and the edges of the two polymer sheets are heat-bonded to seal the gel within a continuous thermopolymer sheet bladder.

When drawn under heat and vacuum, the drawn thermopolymer sheet portion(s) will be made thinner than the starting stock material. One of skill in the art will recognize the effects of vacuum drawing on thermopolymer sheet thickness. For particular applications, one of skill in the art may select polymer sheets having varying thicknesses. For example, a thinner film will maximize the ability for the filled bladder to contour. Thicker films must be used for deeper draws in the heated mold.

In instances having one or more local lobes 42, as, for example, in FIGS. 3 and 4, the cavity of the molding apparatus contains a local cavity (i.e., a cavity deeper than the cavity forming adjacent non-lobe portions) deepening the draw to form the one or more local lobes 42. As discussed in connection with FIG. 13, local lobe(s) have an upper portion and a lower portion. The upper and lower portion of local lobe(s) 42 may be alternatively referred to herein as local lobe domains 42. The upper portion of local lobes 42 are both local and prominent, rising dramatically from the non-lobe portions of the sealing element 43. As indicated elsewhere, the location of the local lobes corresponds with areas of dramatic feature change in the contour of a face to be fit (e.g., around the nose and the bridge of the nose).

Figure 12:
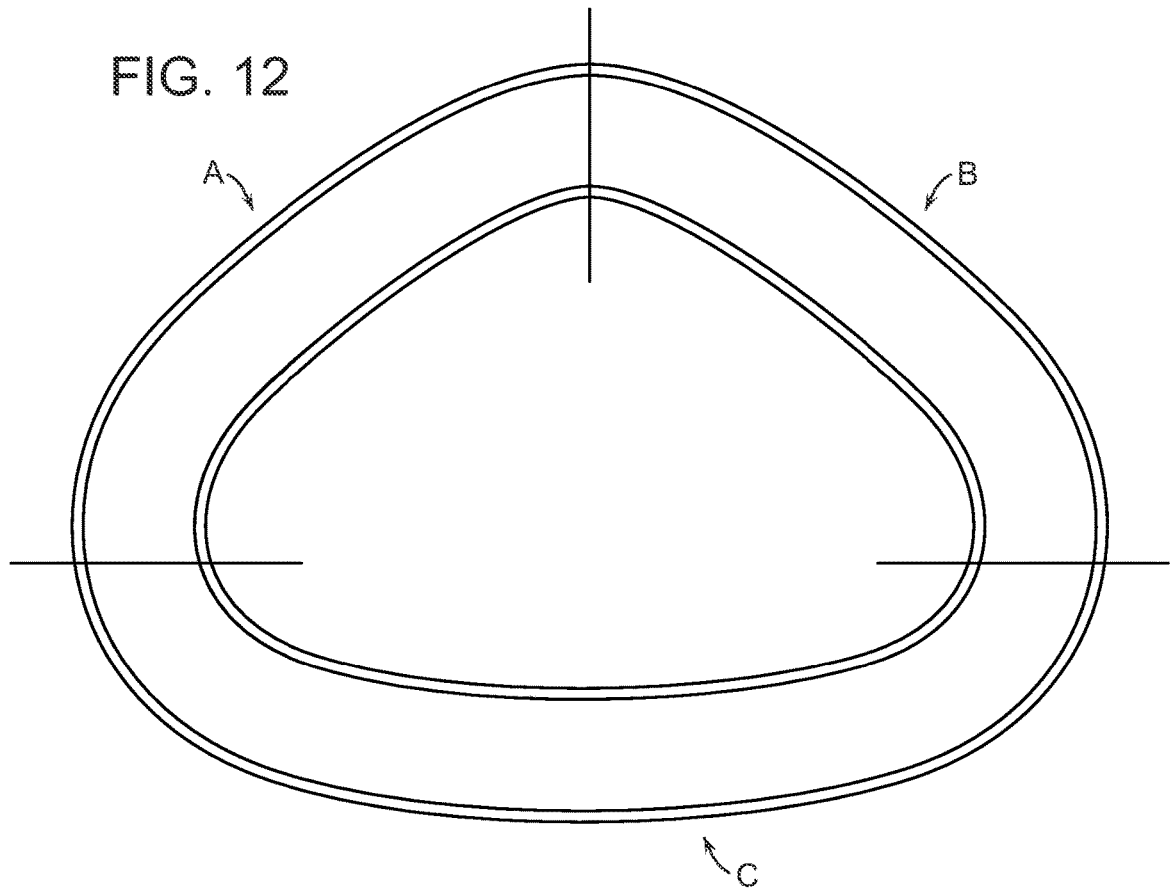
FIG. 12 is a top projection view of an instance of the sealing element of the present disclosure.

FIG. 12 is a top projection view of a sealing element 43 of the present disclosure. The seal of the present disclosure can be viewed as comprising 3 segments: A, B and C. Segments A and B are designed to seal an area of the face extending from the nose and the bridge of the nose at the intersection of segments A and B, and extending down to the sides of the mouth defined by the two termini of segment C.

Figure 13:
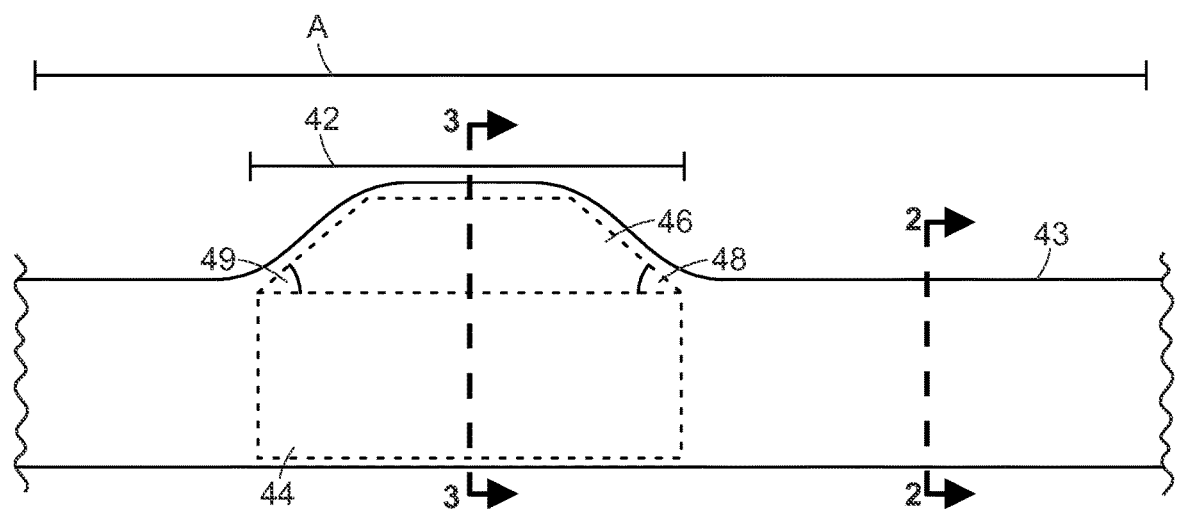
FIG. 13 is a side projection view of an instance of the sealing element of the present disclosure taken along Segment A in FIG. 12.

FIG. 13 shows a side projection view along segment A of FIG. 12, including a local lobe domain 42. As can be seen, the upper portion of the local lobe rises dramatically from the adjacent non-lobe portions of the sealing element 43.

The upper portion of the local lobes 42 rising from the adjacent non-lobe portions of the sealing element 43 tend to be trapezoidal in shape based on the manufacturing process (discussed elsewhere herein). As shown in FIG. 13, the side projection of the local lobe 42 can be broken down into a generally rectangular (or lower) portion 44 the height of which approximates the height of side projections of adjacent non-lobe portions of the sealing element 43, and a generally trapezoidal portion 46 sitting atop the rectangular portion 44. The trapezoidal portion 46 represents the local lobe 42 rising dramatically from the adjacent non-lobe portions of the sealing element 43. The angled side legs of the trapezoid form an average angle 48 and 49 with the top of the rectangular portion 44 and the average angle 48 and 49 is preferably between 30 degrees and 89 degrees. One of skill in the art will recognize that average angles 48 and 49 can differ dramatically from one another, but will fall within the preferred range of 30 degrees to 89 degrees.

In designing the local lobes, one of skill in the art will recognize and consider several important design factors. The lobe must be large enough to seal around features of the face with dramatic structural changes. An example given previously is the nose and the bridge of the nose. It will also be recognized that lobes that are too large will also result in a "leaky" seal caused by the upper portion of the local lobe 42 lifting the adjacent non-lobe portion off the face.

Figure 10:
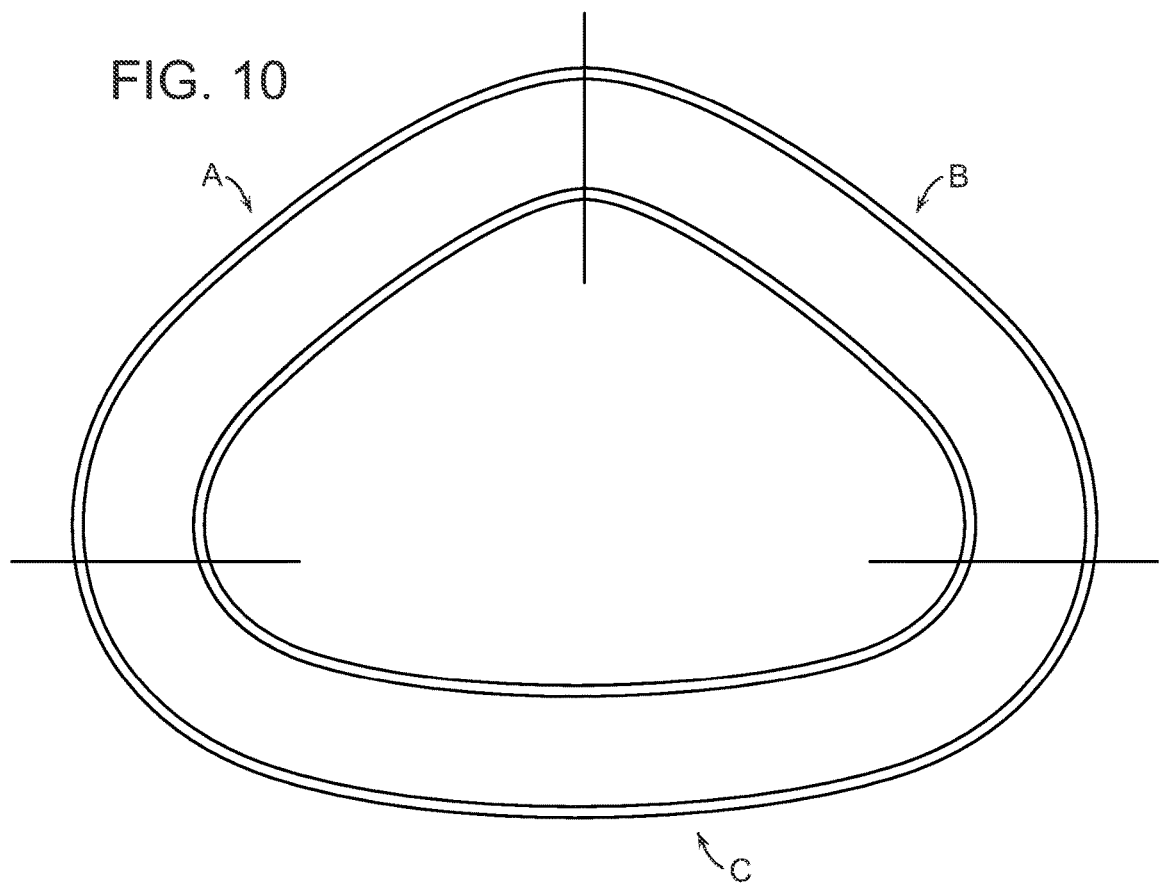
FIG. 10 is a top projection view of an instance of the prior art sealing element.
Figure 11:
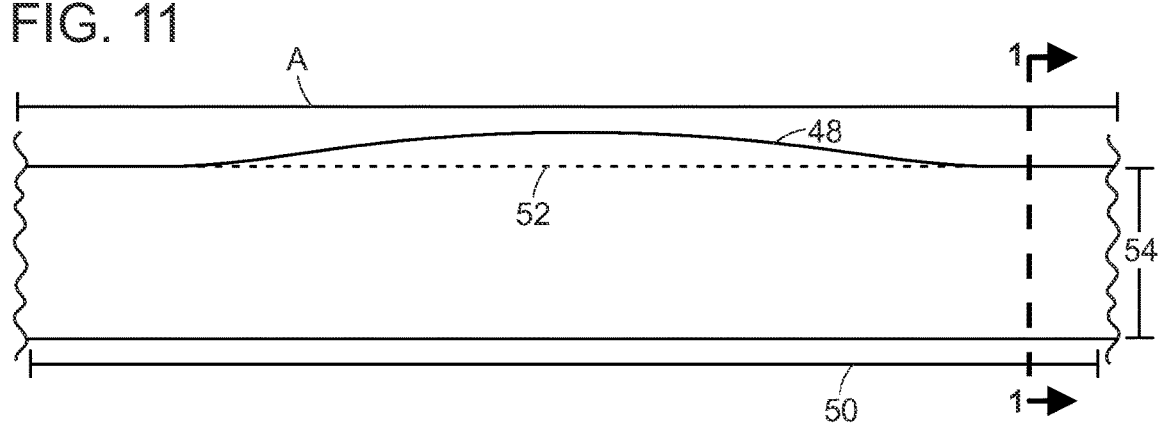
FIG. 11 is a side projection view of an instance of the prior art sealing element taken along Segment A in FIG. 10.

As discussed elsewhere, and depicted diagrammatically in FIG. 1, certain instances of prior art sealing elements can be described as "U-shaped" or "modified or extended semicircular shaped". FIG. 10 shows a top projection view of such a prior art seal. This prior art seal can be viewed as comprising 3 segments: A, B and C. Some instances of such prior art seals have been designed to include one or more mildly sloping raised portions as shown, for example in FIG. 11, which represent a side projection of segment A from FIG. 10. This mildly sloping raised portion can be viewed as a portion of a segment 50 with an arc 48 whose cord length 52 is 50% or more of the segment length 50 (segment A) and the peak of the arc extends 10-100% of the base height 54 of the prior art seal.

Silicone gel is the preferred material for filling the thermopolymer bladder of the sealing element of the present disclosure. The silicone gel material of the present disclosure, when formed into the sealing element of the present disclosure, has a durometer value of 60 or less on a Type 000 Shore scale; a durometer value of 50 or less on a Type 000 Shore scale; a durometer value of 40 or less on a Type 000 Shore scale; a durometer value of 30 or less on a Type 000 Shore scale; a durometer value of 20 or less on a Type 000 Shore scale or a durometer value of 10 or less on a Type 000 Shore scale.

Other materials, as discussed above, are also suitable for the use as the sealing element of the present disclosure. Other materials may or may not require a bladder. For example, foam or rubber may be molded or otherwise shaped (e.g., by cutting) without the need for a bladder.

As shown in FIGS. 3 and 4, the sealing element of the present disclosure may further comprise one or more local lobes 42 extending the skin contact face 31 and the third face 32 for sealing areas of substantial variation in facial structure of the user. For example, on a mask that covers the nose and mouth, but not the eyes, local lobes 42 may be located at the portion of the sealing element that positions on either side of the nose and the bridge of the nose to compensate for the extreme change in contour of the face at this position. As mentioned elsewhere, the expressions "local lobe" and "local lobe domain", singular or plural, may be used interchangeably herein. Likewise, local lobes may be advantageous on sealing elements used on nasal and facemasks covering the eyes, as well as the nose and mouth, as areas of substantial variation in facial structure can vary depending on the type of mask used. For example, nasal masks may require local lobes on either side of the nose and the bridge of the nose and facemasks covering the eyes may require local lobes adjacent to the eye sockets, under the lower lip or at the cheeks. As shown in FIG. 3, the local lobe domain 42 comprises a skin contact face 31, an attachment face 33 and a third face 32. As discussed elsewhere, the area of transition 34 between the skin contact face 31 and the third face 32 tends to resemble a rounded transition, or even a flat spot, due to manufacturing techniques. In essence, the local lobe extends the third face 32 and the skin contact face 31 proportionally thereby maintaining the profile of the adjacent non-lobe regions.

Figure 5:
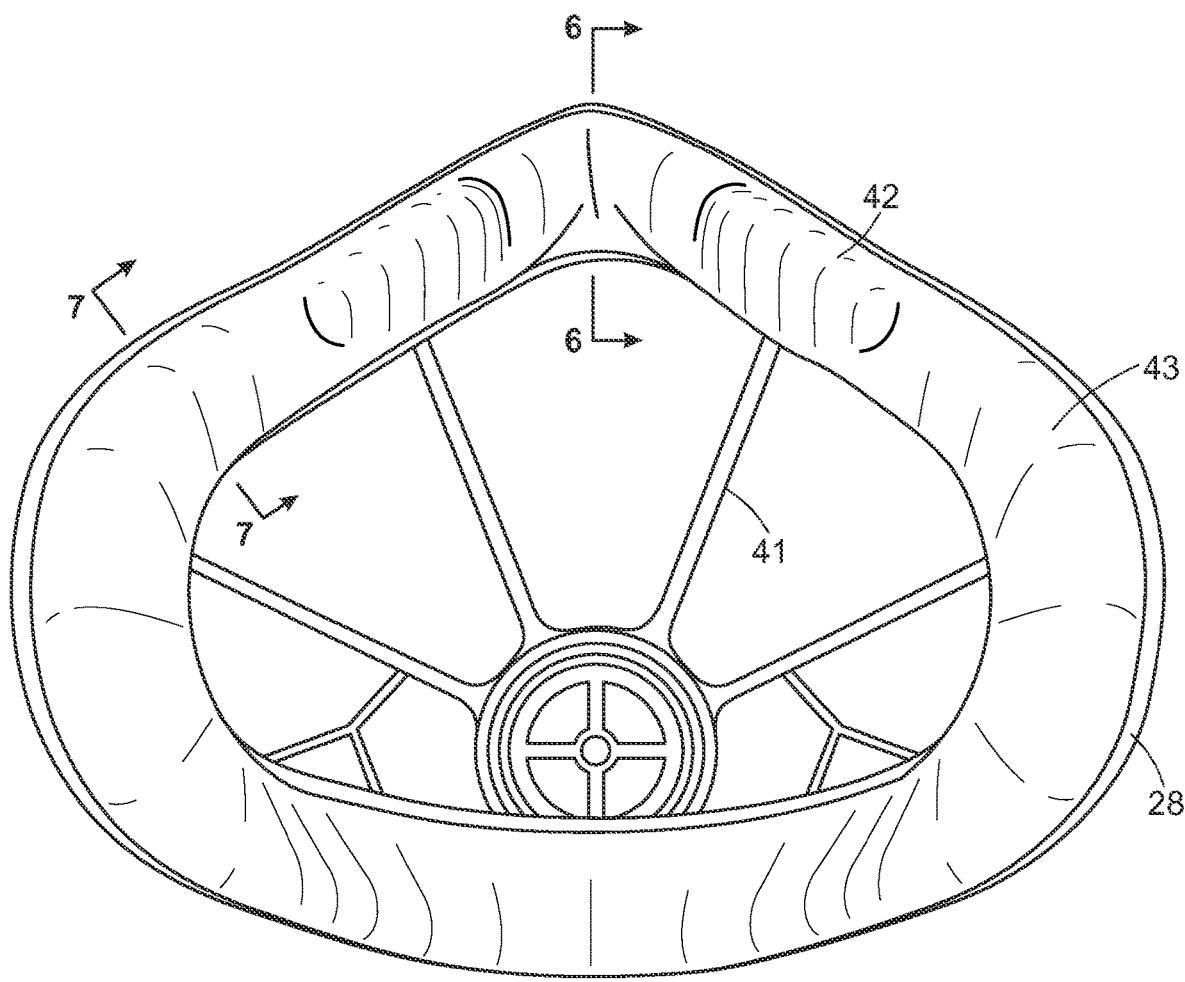
FIG. 5 shows a rear view of a facemask with an instance of the sealing element of the present disclosure.
Figure 6:
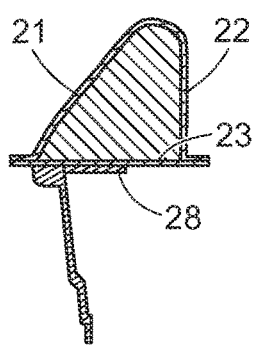
FIG. 6 shows a cross-sectional view of an instance of the sealing element of the present disclosure attached to the attachment flange of the facemask taken through line 6-6 of FIG. 5.

In another instance, the present disclosure relates to a facemask (e.g., nasal or other facemask, as described above) comprising a sealing element of the present disclosure, as described above and exemplified herein. As shown in FIGS. 4 and 5, the facemask may have, for example, a housing that defines a chamber 41, the housing comprising a continuous facemask attachment flange 28, the continuous facemask attachment flange being located, for example, at the periphery of the chamber. The facemask attachment flange is also shown in cross-section in FIGS. 6 and 7. The sealing element 43 of the present disclosure is attached to the facemask attachment flange 28 via the attachment face (e.g., 23 and 33) of the sealing element thereby being configured to form a seal between the attachment flange of the facemask housing and the face of a user. The sealing element of the present disclosure may be attached to the attachment flange with any method known to one of ordinary skill in the art such as, for example, adhesive and/or heat. The attachment flange 28 is perhaps shown best in the exploded perspective of FIG. 14. In FIG. 14, the sealing element 43 is depicted as detached from the attachment flange 28.

Figure 7:
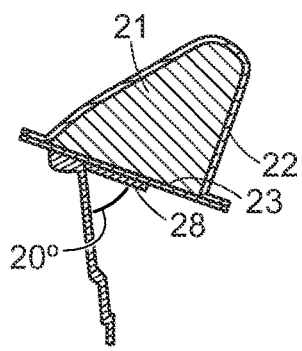
FIG. 7 shows a cross-sectional view of an instance of the sealing element of the present disclosure attached to the attachment flange of the facemask taken through line 7-7 of FIG. 5.
Figure 9:
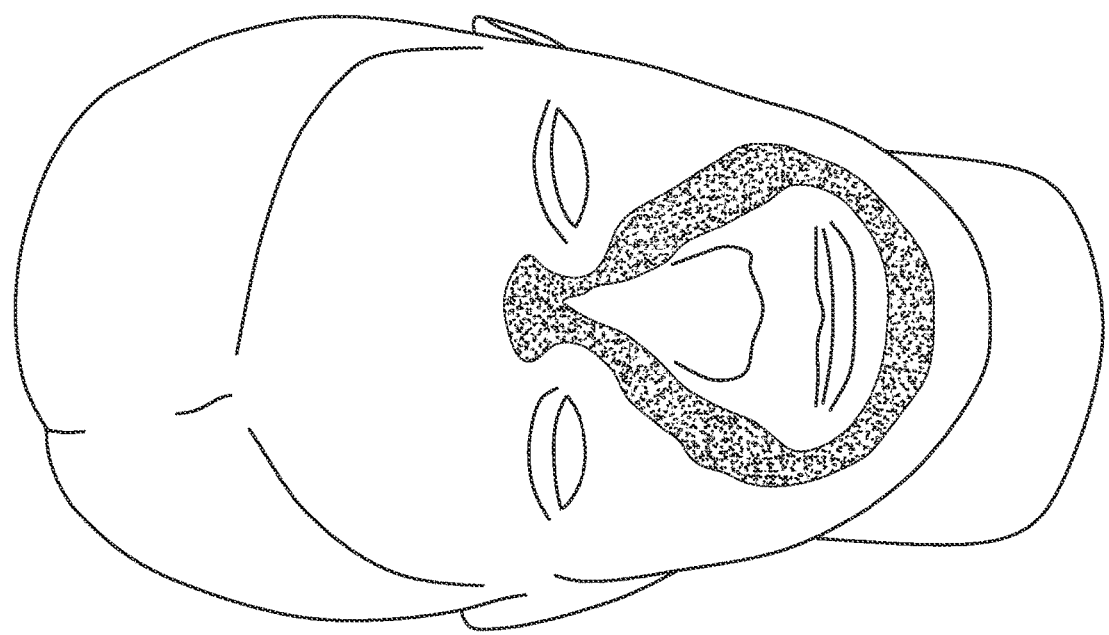
FIG. 9 shows the contact area made by an instance of the sealing element of the present disclosure when positioned on a display head.
Figure 8:
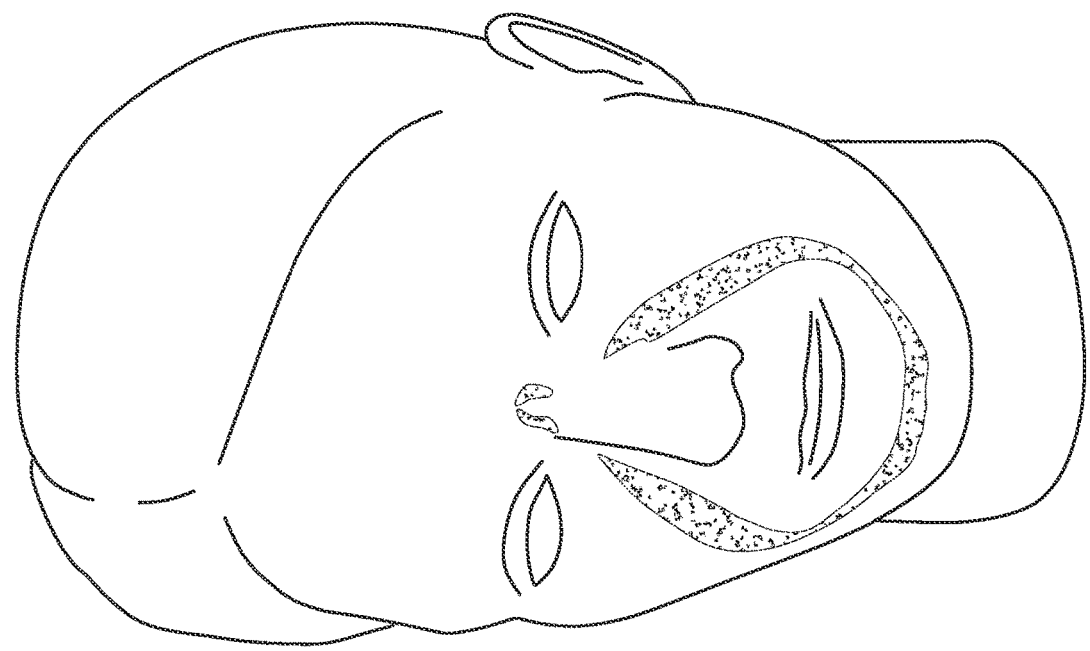
FIG. 8 shows the contact made by an instance of the prior art seal when positioned on a display head.

As shown in FIG. 7, a portion of the attachment flange 28 of the facemask is angled to slope inwardly along at least a majority of its surface length. The inwardly sloping attachment flange aids in the positioning of the sealing element of the present disclosure to ensure that the skin contact face 21 of the sealing element makes maximum contact with the user's face. The superior contact and seal provided by the sealing element of the present disclosure versus the prior art sealing element are shown diagrammatically in FIGS. 8 (prior art seal) and 9 (sealing element of the present disclosure). The materials and methods utilized to generate the data depicted diagrammatically in FIGS. 8 and 9 is set forth in the Exemplification section which follows.

The portion (percent) of the length of the attachment flange that slopes inwardly depends on the type of mask used (e.g., nasal or facemask type as discussed above). In any event, the percent of the attachment flange that slopes inwardly is at least 75%; at least 65%; at least 55% or at least 50% of its surface length. The attachment flange slopes inwardly at least 5 degrees; at least 10 degrees; at least 15 degrees; at least 20 degrees; at least 25 degrees or at least 30 degrees. The attachment flange slopes inwardly from about 5 degrees to about 30 degrees, from about 10 degrees to about 30 degrees or about 15 degrees to about 30 degrees. In one aspect, for example, for a facemask covering only the nose and mouth, the sides of the mask (i.e., the portions relative to the seal that contact a user's cheeks) angle inwardly to a greater extent than at the top and bottom of the mask (i.e., the portions relative to the seal that contact a user's nose bridge and chin, respectively). A non-angled portion of an attachment flange is shown in cross-section in FIG. 6. This portion of the attachment flange 28 is position above the bridge of the nose, for example.

The sealing element of the facemask of the present disclosure comprises at least three primary external face as, as described above. The sealing element of the facemask of the present disclosure forms a seal between the skin contact face of the sealing element of the facemask and the face of the user when worn by the user. The surface area of the seal formed between the skin contact face of the sealing element of the present disclosure and the face of the user is greater than the surface area formed by an otherwise identical facemask having a semi-circular or modified semi-circular (described in the Exemplification section, below) sealing element of substantially identical height (but less volume). Further, the surface area of the seal formed between the skin contact face of the sealing element of the present disclosure and the face of the user is greater than the surface area formed by an otherwise identical facemask having a semi-circular or modified semi-circular (described in the Exemplification section, below) sealing element of substantially identical volume (but greater height).

The sealing element of the facemask of the present disclosure can be comprised of one or more formed flexible materials having a durometer value of 60 or less on a Type 000 Shore scale; a durometer value of 50 or less on a Type 000 Shore scale; a durometer value of 40 or less on a Type 000 Shore scale; a durometer value of 30 or less on a Type 000 Shore scale; a durometer value of 20 or less on a Type 000 Shore scale or a durometer value of 10 or less on a Type 000 Shore scale. Exemplary formed flexible materials suitable for use in the sealing element of the present disclosure are, for example, silicone gel, foam (of various types known to one of ordinary skill in the art) and rubber (natural or synthetic).

Exemplification

Summary

The seal formed between a user's face and a triangular instance of the sealing element of the present disclosure was studied and characterized. The seal, studied and characterized in this manner, was compared with a seal formed between a user's face and a prior art semi-circular seal having a volume approximating that of the triangular instance of the sealing element of the present disclosure. The footprint density of the seal formed by the triangular instance of the sealing element of the present disclosure was estimated to be 80%-100% greater than the footprint density of the semi-circular seal having a volume approximating that of the triangular instance of the sealing element of the present disclosure.

Materials and Methods

The seal formed between a user's face and an instance of the sealing element of the present disclosure was studied using a male display head in white from Zing Display (28562 Oso Parkway D136, Rancho Santa Margarita, CA). A facemask frame, including an attachment flange as described herein, was fitted with an instance of the sealing element of the present disclosure. A cross-section of the sealing element of the present disclosure was triangular in configuration. More specifically, it was a triangular configuration with the third face having a length of 0.66 inches, a skin contact face having a length of 0.82 inches and an attachment face having a length of 0.69 inches. The height of the sealing element was 0.55 inches. The volume of the sealing element of the present disclosure was 61 ml.

The seal formed between a user's face and a prior art modified semi-circular sealing element of was studied using an identical male display head in white from Zing Display. A facemask frame, as described in the previous paragraph, was fitted with the prior art sealing element. The height of the modified semicircular sealing element was 0.5 inches. The volume of the prior art sealing element was 52.6 ml. As indicated, an effort was made to compare sealing elements of substantially identical volume and height, but due to molding considerations, some differential was necessary. Specifically, the sealing element of the present disclosure had a volume approximately 16% greater, and a height approximately 10% greater than the prior art sealing element. This difference was deemed acceptable and is taken into account when interpreting results.

Both the sealing element instance of the present disclosure and the sealing element of the prior art comprise an external membrane made from a first and a second thermopolymer sheet portion containing a silicone gel having a durometer value of approximately 10 using 000 Shore scale. Both sealing elements were attached to a substantially identical facemask frame having an attachment flange which sloped inwardly at about 0 to 25 degrees along the mask to contour to a typical face.

The skin contact face of the sealing element of the present disclosure and the semi-circle arc of the prior art sealing element were marked using a black lipstick. Lipstick applied in this manner was demonstrated to transfer, upon contact, with the display head. With regard to the sealing element of the present disclosure, application of the lipstick to the third face was avoided to prevent false readings that may be caused when the third face inadvertently moved while being positioned on the display head. Further, lipstick was not applied to some area of the sealing element to avoid the fingerprint effect of making an impression where only intermittent contact was made during positioning of the mask. Some judgement was used here by observing how the sealing element rested on the manikin after reaching maximum contact.

Following application of the lipstick, the sealing elements were brought into contact with the display heads, mimicking use. Downward force (i.e., in a vector toward the face of the display head) was applied to each facemask frame making each sealing element pivot (i.e., roll towards the center of the mask) to its maximum angle, similar to when worn by a user. The black lipstick was transferred to the display heads leaving a record of the contact surface area for each sealing element. Both sealing elements transferred wax to the display head remarkably well.

Results

The density of wax transfer to display heads using each of the sealing elements was estimated to be 80%-100% greater for the sealing element of the present disclosure as compared with the prior art sealing element. This visual estimate can be confirmed by photographic densitometry measurements. Graphic representations of the wax transfer observations are shown in FIG. 8 (prior art sealing element) and FIG. 9 (sealing element of the present disclosure). Aside from the visual density estimates, it can be seen in FIG. 8 that the prior art sealing element failed to make contact in areas around the nose and the bridge of the nose. FIG. 9 shows good contact in trouble areas such as the area around the nose and the bridge of the nose and the corners of the mouth.

The density of the wax transfer and overall quality of the contact observed with the triangular sealing element of the present disclosure was surprising when compared with the prior art modified semi-circular sealing element observations. Although the volume of the triangular sealing element of the present disclosure was approximately 16% greater than the volume of the prior art modified semi-circular sealing element, and the height of the triangular sealing element of the present disclosure was approximately 10% greater than the height of the prior art modified semi-circular sealing element, these differences alone do not account for the dramatic increase in lipstick transfer.

FIG. 15 is a graphic representation which depict the sealing element of the present disclosure with the skin contact face making contact with the skin. As contact is made, the third face bulges and the skin contact face "lays down" increasing the contact area with the face. FIG. 16 is a graphic representation which depicts the prior art sealing element (modified semi-circular) making contact with the skin. The triangular shape of the seal of the present disclosure allows for the skin contact face to "lay down" (or redirect) allowing the majority of the surface of the plane to make contact and remain in contact with the user's face. As discussed above, the modified prior art semi-circular sealing element of the prior art forms an inferior seal.

We claim:

1. A sealing element of a facemask, comprising:
a formed flexible material that is substantially triangular in cross-section, the formed flexible material containing a fluid or gel within an entirety of the substantially triangular cross-section, the formed flexible material having three primary faces comprising:
a facemask attachment face;
a skin contact face; and
a third face, wherein the skin contact face is substantially planar and the third face is substantially planar, wherein the
facemask attachment face is configured to contact an attachment surface of the facemask,
wherein the skin contact face is a longest of the three primary faces when the sealing element is viewed in cross-section,
wherein the third face extends from a plane defined by the attachment surface,
wherein, when the sealing element is viewed in cross section, the third face has a length that is less than 90% of a length of the skin contact face,
wherein an entirety of the third face is configured to form a portion of an interior of a facemask chamber when the facemask is worn by a user, and
wherein the third face is configured to be part of an airway passage of the facemask when the facemask is worn by the user.

2. The sealing element of claim 1, wherein the formed flexible material is configured to fit over:
a nose of the user;
the nose and a mouth of the user;
the nose, the mouth, and eyes of the user; or
the nose, the mouth, the eyes, and a chin of the user.

3. The sealing element of claim 1, wherein the formed flexible material has a durometer value of 60 or less on a Type 000 Shore scale.

4. The sealing element of claim 1, wherein the formed flexible material is formed from at least one thermopolymer sheet.

5. The sealing element of claim 1, wherein the gel is silicone gel.

6. The sealing element of claim 1, wherein the length of the third face is less than 70% of the length of the skin contact face.

7. The sealing element of claim 1, wherein an angle formed between the facemask attachment face and the third face is between 70 degrees and 90 degrees.

8. The sealing element of claim 1, wherein the formed flexible material further has a local lobe configured to create a seal around a nose of the user.

9. The sealing element of claim 1, wherein:
the third face occupies an inner perimeter of the sealing element; and
the skin contact face occupies an outer perimeter of the sealing element.

10. The sealing element of claim 1, wherein the third face becomes un-planar and expands into the airway passage when the skin contact face is contacted with the user's face.

11. A method for making a sealing element of a facemask, comprising:
drawing a first thermopolymer sheet into a molding apparatus with heat and vacuum to form a cavity;
placing a fluid or gel within the cavity;
after placing the fluid or gel, overlaying a second thermopolymer sheet on the cavity; and
heat-bonding edges of the first thermopolymer sheet to the second thermopolymer sheet to create a formed flexible material that is substantially triangular in cross-section, the formed flexible material containing the fluid or gel within an entirety of the substantially triangular cross-section, the formed flexible material having three primary faces comprising:
a facemask attachment face;
a skin contact face; and
a third face, wherein the skin contact face is substantially planar and the third face is substantially planar, wherein the
facemask attachment face is configured to contact an attachment surface of the facemask,
wherein the skin contact face is a longest of the three primary faces when the sealing element is viewed in cross-section,
wherein the third face extends from a plane defined by the attachment surface,
wherein, when the sealing element is viewed in cross section, the third face has a length that is less than 90% of a length of the skin contact face,
wherein an entirety of the third face is configured to form a portion of an interior of a facemask chamber when the facemask is worn by a user, and
wherein the third face is configured to be part of an airway passage of the facemask when the facemask is worn by the user.

12. The method of claim 11, wherein placing the gel further comprises placing a silicone gel.

13. The method of claim 11, further comprising:
drawing the first thermopolymer sheet to further form at least one local lobe configured to create a seal around a nose of the user.

14. The method of claim 11, further comprising heat-bonding the edges to create the formed flexible material to be configured to fit over:
a nose of the user;
the nose and a mouth of the user;
the nose, the mouth, and eyes of the user; or
the nose, the mouth, the eyes, and a chin of the user.

15. The method of claim 11, wherein the formed flexible material has a durometer value of 60 or less on a Type 000 Shore scale.

16. The method of claim 11, wherein the length of the third face is less than 70% of the length of the skin contact face.

17. The method of claim 11, wherein an angle formed between the facemask attachment face and the third face is between 70 degrees and 90 degrees.

18. The method of claim 11, wherein:
the third face occupies an inner perimeter of the sealing element; and
the skin contact face occupies an outer perimeter of the sealing element.

* * * * *